United States Patent [19]

Paniagua

[11] Patent Number: 4,572,775
[45] Date of Patent: Feb. 25, 1986

[54] APPARATUS FOR STERILIZING FLUIDS

[76] Inventor: Juan G. Paniagua, Alejandrina N. 1609 Guadalajara, Jalisco, Mexico

[21] Appl. No.: 346,304

[22] Filed: Feb. 5, 1982

[51] Int. Cl.[4] .................... C25B 15/02; C25B 15/08; B01D 35/06
[52] U.S. Cl. ................... 204/229; 204/276; 204/152; 204/306; 210/143; 210/223
[58] Field of Search .............................. 210/222–223, 210/97, 143; 204/229, 228, 152, 275–276, 131, 306

[56] References Cited

U.S. PATENT DOCUMENTS

| | | | |
|---|---|---|---|
| 447,585 | 3/1891 | Schroeder | 204/276 |
| 661,340 | 11/1900 | Grever | 204/229 |
| 951,311 | 3/1910 | Hartman | 204/152 |
| 1,217,365 | 2/1917 | Talley | 204/229 X |
| 2,046,467 | 7/1936 | Krause | 204/229 X |
| 3,095,365 | 6/1963 | Green | 204/229 |
| 3,379,637 | 4/1968 | O'Brien | 210/222 X |
| 3,714,037 | 1/1973 | Almasi et al. | 210/223 X |
| 3,826,035 | 7/1974 | Paniagua | 43/98 |
| 4,119,517 | 10/1978 | Hengst | 204/152 X |
| 4,248,684 | 2/1981 | Doniat | 204/152 X |

*Primary Examiner*—Donald R. Valentine
*Attorney, Agent, or Firm*—Ladas & Parry

[57] ABSTRACT

Bacteria-containing liquids are sterilized by a method and apparatus which employs electrical current to kill the bacteria. The liquid is caused to flow as a stream in a conduit, and a controlled amount of the electrical current is passed laterally through the stream along a given length of the stream path downstream of a stream location where the flowing condition of the liquid is sensed to initiate the passage of the electrical current. Thus, electrical current is only passed through the liquid after it has been first determined that its liquid is flowing. Provision is also made in the method and apparatus to filter large particles from the flowing liquid at least before the liquid is subjected to the passage of the electrical current therethrough.

6 Claims, 16 Drawing Figures

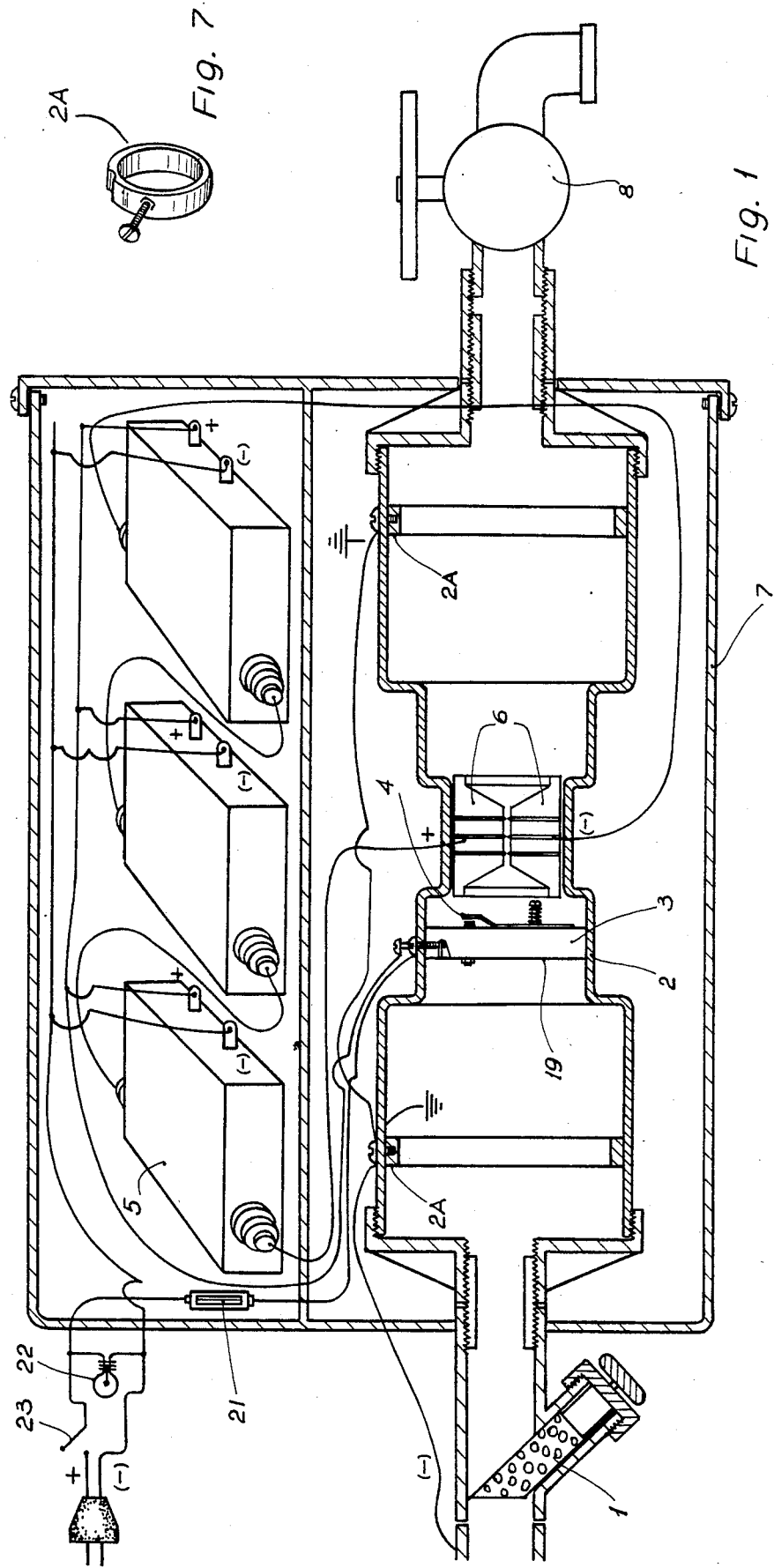

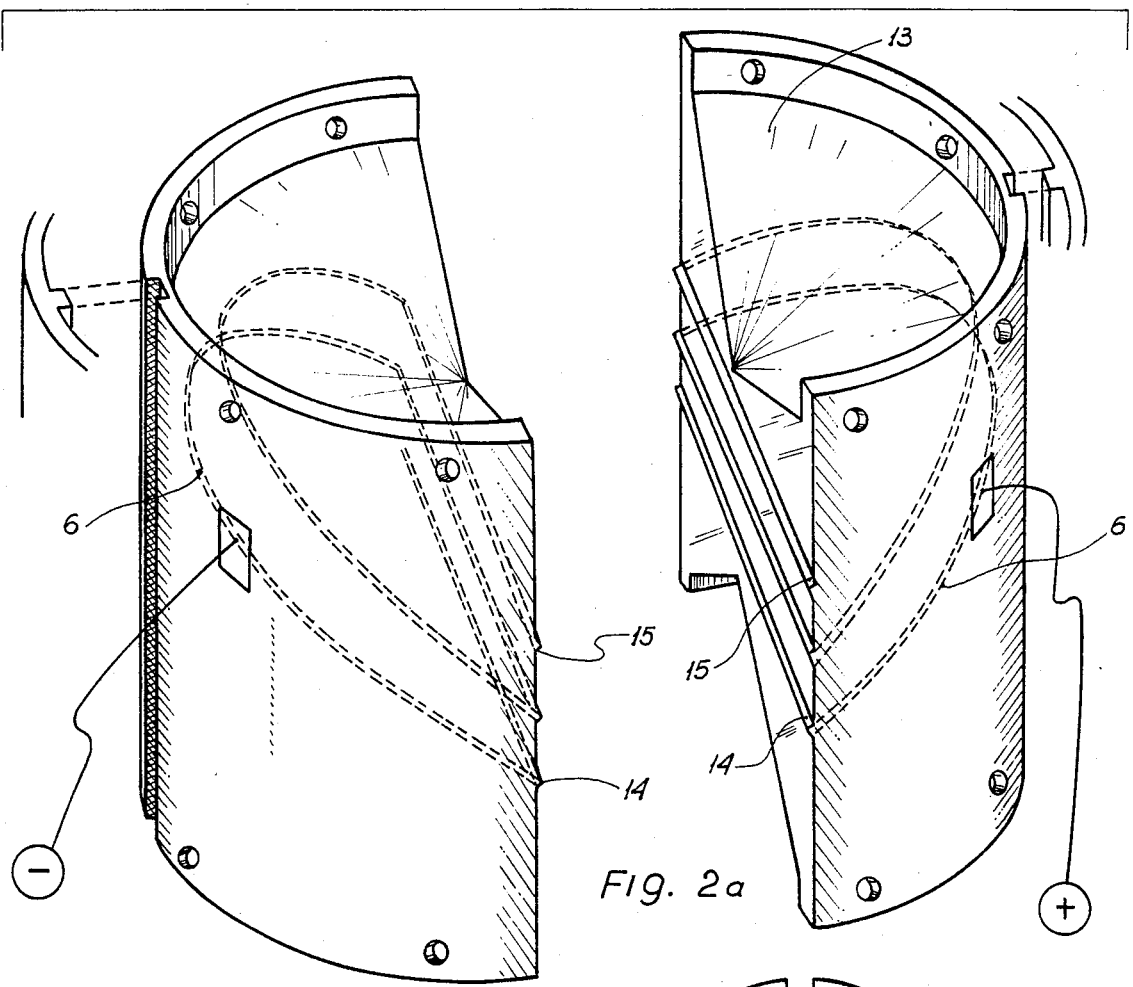
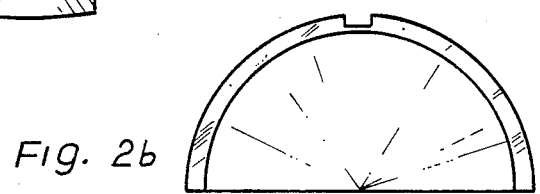
Fig. 2b
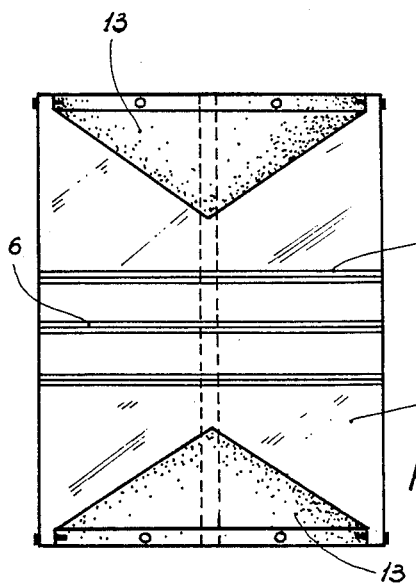
Fig. 2c
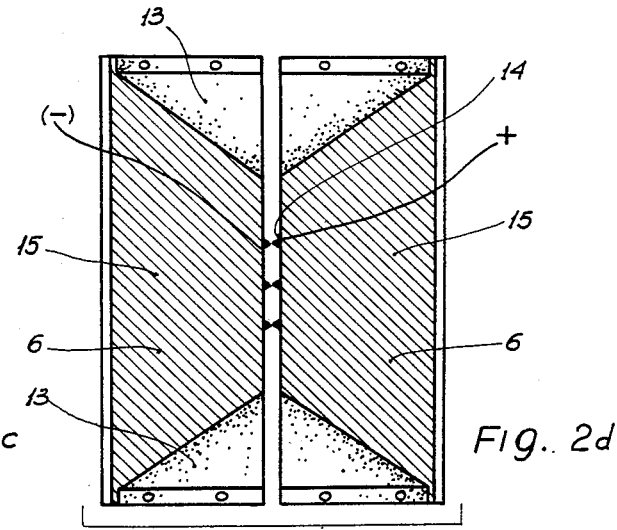
Fig. 2d

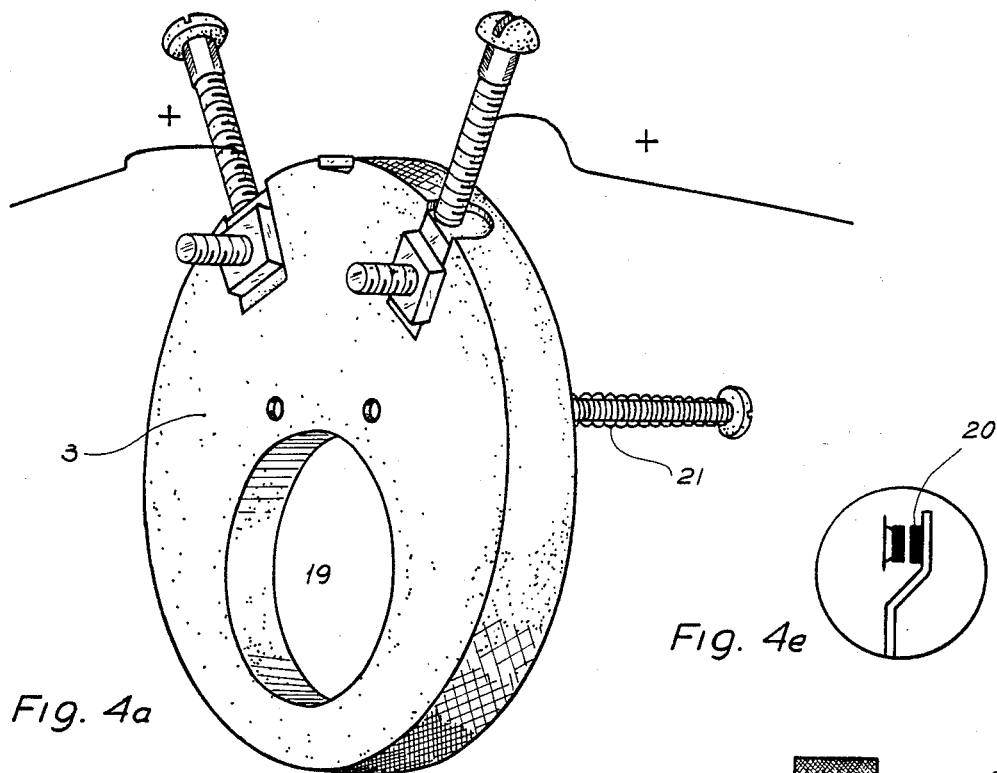
Fig. 4a
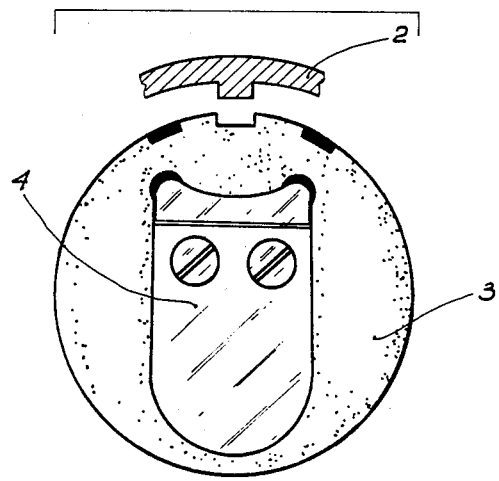
Fig. 4b
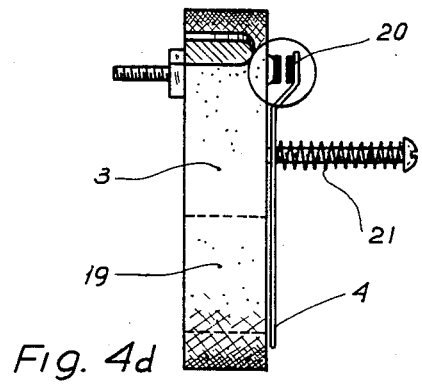
Fig. 4e
Fig. 4d
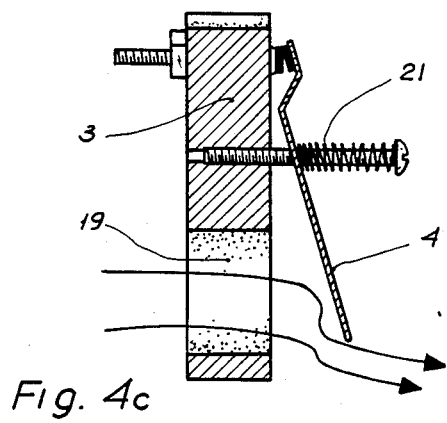
Fig. 4c

APPARATUS FOR STERILIZING FLUIDS

This invention relates to the sterilization of bacteria-containing liquids.

Health control is a field of major importance in the modern world. It has prompted an attempt to control and improve the quality of food products to prevent the spreading of diseases. It has also been of major importance in the field of keeping perishable foodstuffs stored a given time period for later consumption. Pasteurization has achieved worldwide use to the benefit of everyone concerned. However, it has several disadvantages since, on the one hand it does not kill all the bacteria present in the treated medium, and on the other hand is not readily available for treating all types of liquids. It is a generally accepted fact that not all the water distributed in a city water supply system is thoroughly freed from unwanted living organisms, even though it is overladen with chemical substances which are not healthy to drink.

Moreover, laboratory needs in general have not been met in the past, whereby bacteria can be killed or by otherwise rendered inocuous to facilitate treatment and controlled conditions in the science field.

In addition, there is a need for improvements in methods and apparatus for killing germs and bacteria in such diverse fluid media as water, milk, beer and other liquids in which sterilization and/or stopping of fermentation is desired. Such improvements would, for example, be of an economic, efficient, dependable and non-polluting nature to achieve complete sterilization.

According to one aspect of the invention, there is provided a method of sterilizing bacteria-containing liquids, comprising the steps of causing such a liquid to flow along a given longitudinal path, filtering large particles from the flowing liquid, sensing the flow of the filtered liquid past a first location in said given path and, in response to the sensing of said flow, passing a controlled electrical current laterally through the flowing liquid over an area between longitudinally spaced second and third locations along said given path downstream of said first location in order to kill the bacteria in the liquid and thereby sterilize the liquid.

According to another aspect of the invention, there is provided apparatus for sterilizing bacteria-containing liquids, comprising a conduit defining a given longitudinal flow path for a bacteria-containing liquid, a filter in the upstream end of the conduit for filtering large particles from the liquid when said liquid flows in the conduit, a flow sensor in the conduit at a first conduit location downstream of said filter for sensing any flow of liquid past said first location, electrical current discharge means located in the conduit between longitudinally spaced second and third conduit locations downstream of said first location and being energizable to pass an electrical current laterally through any liquid between the second and third conduit locations, an electrical current source, and switch means operable by said flow sensor which, in response to the sensing of liquid flow, connects said current source in energizing relationship with said discharge means, said current source being controllable to cause the current passed by said discharge means through the liquid to kill the bacteria in said liquid and thereby sterilize the liquid.

Thus, the present invention contemplates the provision of a complete system to sterilize a liquid from undesired life forms. The apparatus may include a series of passages subjected to controlled parameter electric activity in a conduit for fluid flow having a high-energy concentrating area to discharge a predetermined voltage and thereby kill germs and the like. For this purpose, there may be provided a combination of two conductive material coils having an electric power input having a given direction flow so as to create an intense electric field. Said field is activated when liquid passes therethrough. It is a natural outcome that, the more germs and bacteria present in the fluid, the more the conductivity improves. The outcome of laboratory tests and of research and development have led to the provision of parts and grids to define specific locations to apply the sterilizing electricity.

This has proved to be necessary given the following experiment:

A fish bowl filled with liquid and having two spaced, parallel insulated wires immersed therein with opposed uninsulated ends receiving electricity from a controlled-parameter d.c. electricity source was provided. The uninsulated wire ends formed a danger line that paralyzed, stunned or killed the fish swimming between both wire ends. When the insulation was further removed from the wires, an area of general rectangular configuration through which electricity would pass directly from one pole terminal to the other was formed. A small fish, swimming in the liquid would not at first react to the current flowing therethrough. The fish, however, would react be stunned when passing through the line between the oppositely-located poles. In the light of the above, it has been deemed convenient to provide an area through which all the fluid must flow. In a conduit, therefore, a reduced clearance passage is preferably provided having a specific gap for a controlled electricity flow and a predetermined length to allow for a given flow capability.

In order that the invention in both of its aforesaid aspects may be more fully understood, it will now be described with reference to the accompanying drawings, in which:

FIG. 1 schematically illustrates a preferred embodiment of the present apparatus;

FIGS. 2a, 2b, 2c and 2d show structural details of one form of electrical discharge means suitable for use in the apparatus depicted in FIG. 1;

FIGS. 4a, 4b, 4c, 4d and 4e show structural details of a flow sensor suitable for use in the apparatus depicted in FIG. 1;

FIG. 7 illustrates a component used in FIG. 1.

Figure 3A:
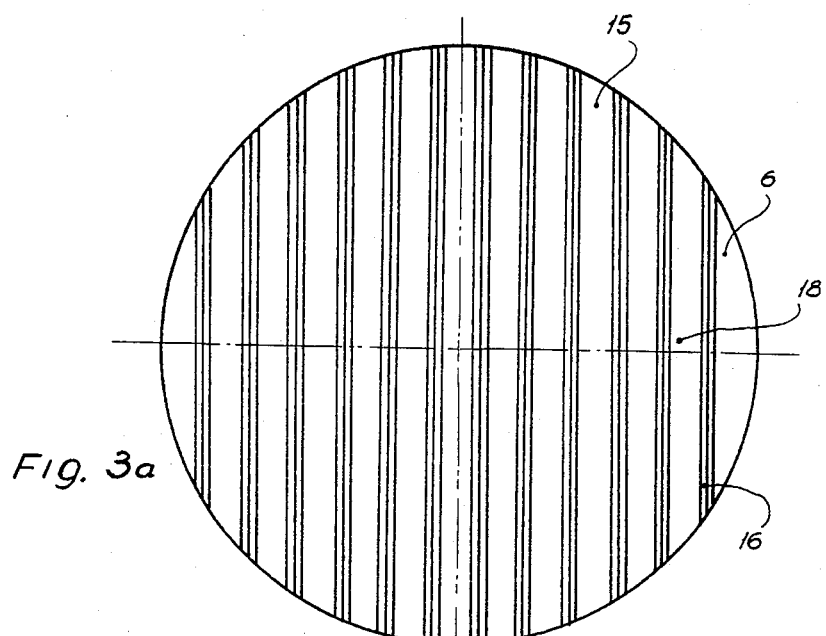
FIGS. 3a, 3b and 3c show structural details of another form of electrical discharge means suitable for use in the apparatus depicted in FIG. 1.

Referring to FIG. 1, the apparatus comprises a conduit to provide fluid passage of a liquid to be sterilized, the conduit having a filter 1 to keep solid particles from flowing in the conduit. The filter 1 is located at the input gate of the conduit. A pair of coils or grids 6 connected to a controlled parameter electrical unit 5 is located downstream of the filter 1. A restricted-flow passage means 2 is connected to the electrical unit 5. A light bulb 22 is connected to the electrical unit 5 to advise when the unit is working. A conduit output gate 8 comprising a valve means is provided to discharge sterilized fluid.

A flow sensor 3 removably obstructs the flow of liquid. When no flow takes place, it disconnects electricity feed, but closes a circuit on flow of fluid, by means of the latter pushing a hinged gate means 4 which in turn bridges two contacts 20 and initiates electricity feed.

The flow of liquid to be sterilized goes through the following steps:

(a) It enters the conduit from a first end thereof,
(b) passes through the filter 1, which may be a mesh or wire netting, to keep big particles from the fluid,
(c) pushes the hinged gate means 4 which closes a circuit and commands the controlled parameter electrical unit 5 to supply electricity to both grids,
(d) reaches the grid area and passes therethrough, under-going the following treatment: (i) distributes itself along a generally rectangular area defined by the two grids 6 which are elongated and separated a uniform distance from one another throughout all the gap, and (ii) on contacting both grids, the liquid closes an electric circuit causing electricity to flow through the liquid, the electric flow killing all unwanted organisms present in the liquid passing through the grids in that instant.

Taking water as the treated medium to prevent confusion when referring to a liquid, fluid and/or electricity flow, the following description details the preferred embodiment which should not be construed as a limitation of the invention.

Downcurrent of the filter 1 is located a grounded ring 2A (see FIG. 7), downcurrent of which is located the flow sensor 3 activated by water flow such that when water flows in the conduit, the gate 4 opens and water flows through the bore 19 in the sensor.

The gate 4 closes an electric circuit and initiates the controlled parameter electrical unit 5 into feeding electricity.

Down current of the sensor 3, there are the grids 6 connected to receive electricity from the controlled parameter electrical unit 5. Water passing through the grids 6 short circuits them and is thereby sterilized.

Downcurrent of grids 6 is located a second grounded ring 2A ensuring there will be no electricity flow coming out through the water outlet 8 located thereafter.

The above referred-to assembly is located within a box 7 made of suitable material. It comprises, moreover, a fuse 21 to protect the electric system, and the light bulb 22 to advise that the system is working, and also a switch 23 to disconnect the system and allow repairs or inspections.

The sterilizing unit 2 comprises a Venturi shaped tube having a stepped inner configuration with a radius that increases from the center thereof to both ends and houses the different devices 3 and 6 according to size.

In FIGS. 2a, 2b, 2c and 2d there are two helicoidal grids 6 formed on respective half cores. Electricity flows through helicoidal grids 6 when the flow sensor 3 initiates electricity flow upon closing the circuit. Water flowing between both half-cores short circuits the electricity fed both grids 6 and is thereby sterilized.

Figure 3B:
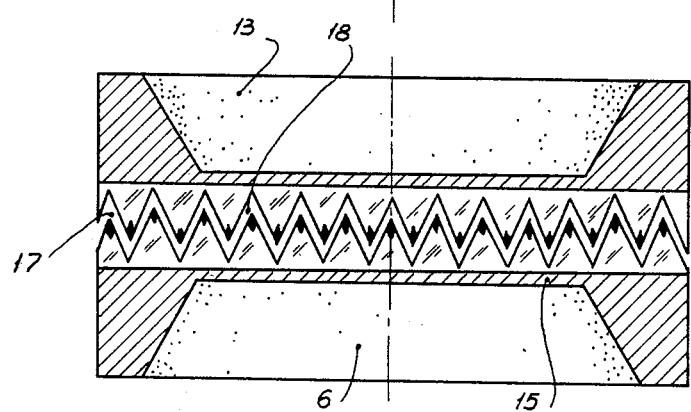
Figure 3C:
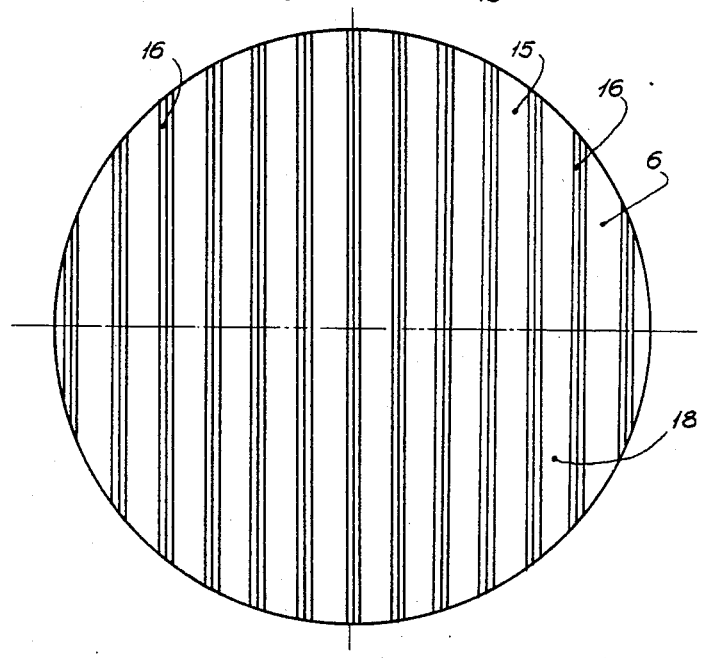

In FIGS. 3a, 3b and 3c of the drawings, there are two oppositely disposed half grids 15, each half grid having several bars 16, each bar 16 having a diamond-shaped cross section 17. When both half-grids are assembled, the edges of the bars form a lineal array of separated bars which form a series of passages 18 for water circulation.

When the bars are electrified, water passing between the bars short circuits the electricity which then kills germs and bacteria in the water.

There is a grounded metallic ring 2A located upstream of grid units 14 or 15 and a second grounded metallic ring 2A located downstream of units 14 or 15, both of which ensure that there will be no electricity in the system, except where it is desired.

Outlet valve 8 may also include a filter unit which may vary according to the liquid to be sterilized and which may be obtained in the market.

In FIGS. 4a, 4b, 4c, 4d and 4e of the drawings, the flow sensor 3 is a solid disc shaped unit comprising an eccentric bore 19 for water passage and the hinged gate means 4 which removably obstructs the bore 19. Gate means 4 comprises two projections, each projection having a suitable metal, or point 20, which contact two corresponding points when the gate means 4 is pushed sideways into an open position by the flow of water, closing the electric circuit and advising there is a water flow. The hinged gate means 4, as shown in FIGS. 4b, 4c and 4d is resiliently kept in a closed position by resilient members 21.

Figure 5:
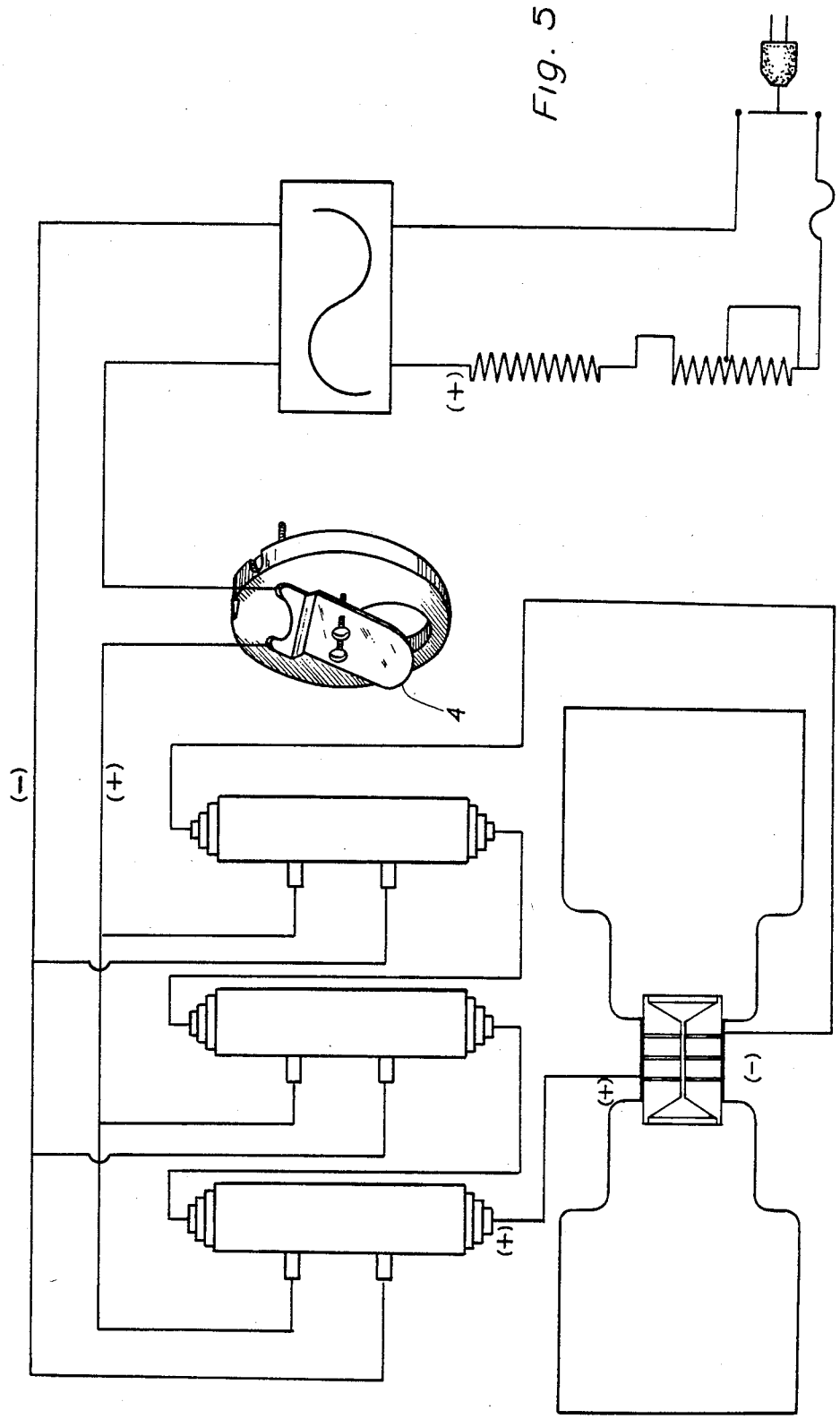
FIG. 5 shows circuitry associated with the electrical current source of the apparatus depicted in FIG. 1; and, FIG. 6 illustrates how the invention may be applied to the sterilization of containers and caps for the containers.
Figure 6:
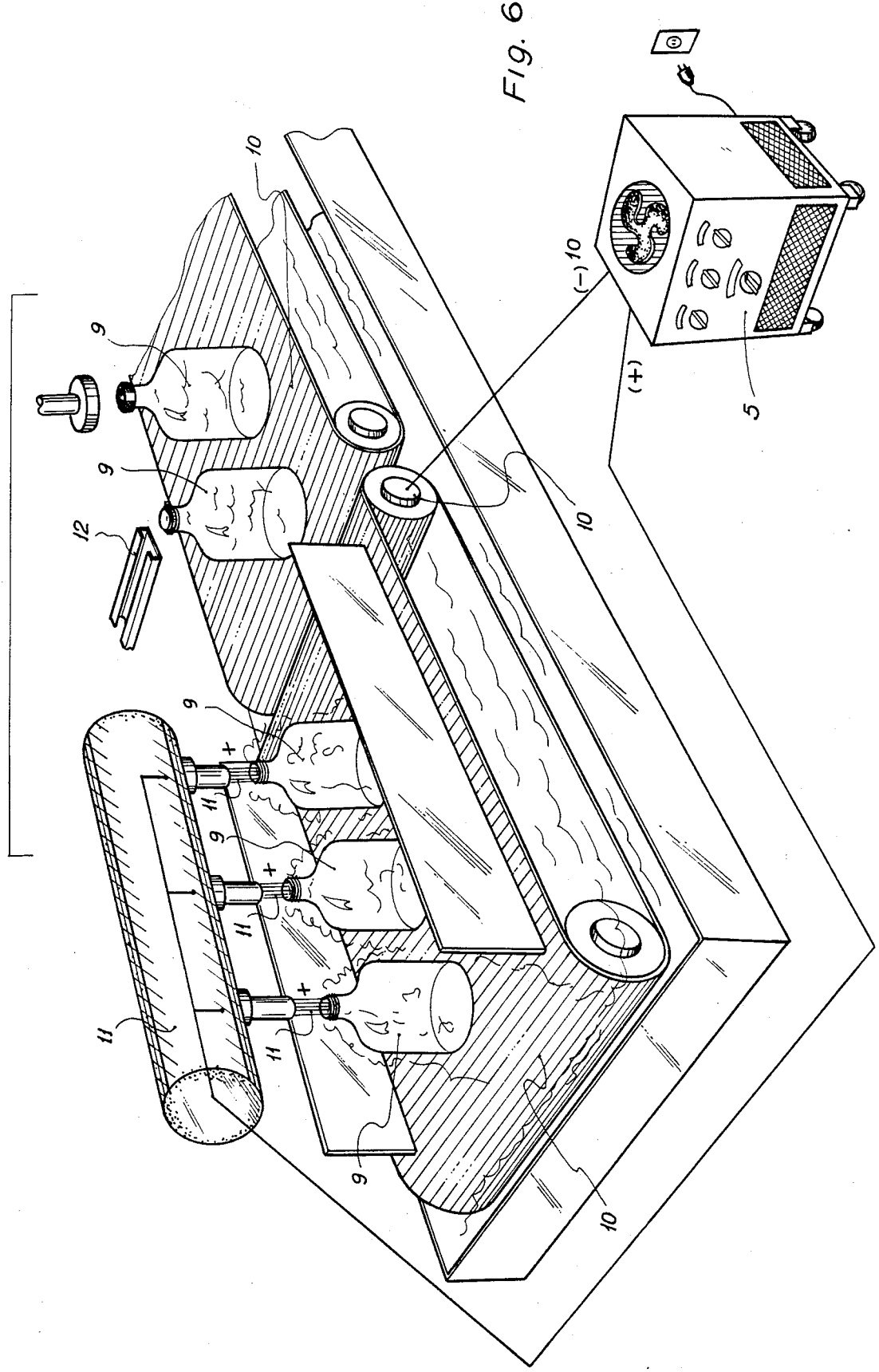

In FIG. 5 of the drawings is shown the circuitry for a low voltage and high voltage feed from the controlled parameter electrical unit 5 corresponding to an application thereof set forth in FIG. 6 of the drawings relating to the container and cap sterilizing embodiment. When the system is used for filling containers 9, the containers are connected to a negative polarity 10, and the liquid being filled into the containers has a positive polarity 11 to sterilize the container and provide a continuous sterilization through the operation of sealing the containers with sterilized caps 12. This provides a complete sterilization even when the water being filled into the containers may displace unsterilized air, attaining a complete sterilization of the water, the container and the cap.

I claim:

1. Apparatus for sterilizing bacteria-containing liquids, comprising a conduit defining a given longitudinal flow path for a bacteria-containing liquid, a filter in the upstream end of the conduit for filtering large particles from the liquid when said liquid flows in the conduit, a flow sensor in the conduit at a first conduit location downstream of said filter for sensing any flow of liquid past said first location, electrical current discharge means located in the conduit between longitudinally spaced second and third conduit locations downstream of said first location and being energizable to pass an electrical current laterally through any liquid between the second and third conduit locations, an electrical current source, and switch means operable by said flow sensor which, in response to the sensing of liquid flow, connects said current source in energizing relationship with said discharge means, said current source being controllable to cause the current passed by said discharge means through the liquid to kill the bacteria in said liquid and thereby sterilize the liquid, the flow sensor including a hinged gate which is arranged to be pivoted out of an obstructing position in the conduit by its force of flowing liquid impinging thereon and into a position that operates the switch means wherein the electrical current discharges means comprises a spaced pair of grids defining a constricted passage for liquid therebetween, each grid being electrically connected to a corresponding output terminal of the electrical current source.

2. Apparatus according to claim 1, wherein each grid comprises a helical coil formed on a respective core.

3. Apparatus according to claim 1, wherein each grid comprises a plurality of bars, each bar having a diamond-shaped cross-section.

4. Apparatus for sterilizing bacteria-containing liquids, comprising a conduit defining a given longitudinal flow path for a bacteria-containing liquid, a filter in the upstream end of the conduit for filtering large particles from the liquid when said liquid flows in the conduit, a flow sensor in the conduit at a first conduit location downstream of said filter for sensing any flow of liquid past said first location, electrical current discharges means located in the conduit between longitudinally spaced second and third conduit locations downstream of said first location and being energizable to pass an electrical current laterally through any liquid between the second and third conduit locations, an electrical current source, and switch means operable by said flow sensor which, in response to the sensing of liquid flow, connects said current source in energizing relationship with said discharge means, said current source being controllable to cause the current passed by said discharge means through the liquid to kill the bacteria in said liquid and thereby sterilize the liquid, the conduit being provided in its interior with two electrically grounded rings, one at the upstream end and the other at the downstream end, to ensure that the electrical current passing laterally through the liquid between the second and third conduit locations will be the only electrical current passing through the liquid during operation of the apparatus wherein the electrical current discharges means comprises a spaced pair of grids defining a constricted passage for liquid therebetween, each grid being electrically connected to a corresponding output terminal of the electrical current source.

5. Apparatus according to claim 1 or 4, wherein the electrical current source is a controlled-parameter d.c. source having a positive output terminal and a negative output terminal.

6. Apparatus according to claim 5, wherein one of the output terminals of the d.c. source is arranged to contact a container at a container-filling station, while the other output terminal is arranged to contact a liquid being filled into the container at the station, whereby continuous sterilization of the liquid and the container is provided throughout a filling operation.

* * * * *